US011926633B2

(12) United States Patent
Wang et al.

(10) Patent No.: US 11,926,633 B2
(45) Date of Patent: Mar. 12, 2024

(54) SYNTHESIS METHODS FOR UPADACITINIB AND INTERMEDIATE THEREOF

(71) Applicant: SUZHOU PENGXU PHARMATECH CO., LTD, Suzhou (CN)

(72) Inventors: Peng Wang, Suzhou (CN); Pixu Li, Suzhou (CN); Qiang Wei, Suzhou (CN); Wen Cheng, Suzhou (CN); Hao Wu, Suzhou (CN)

(73) Assignee: SUZHOU PENGXU PHARMATECH CO., LTD, Suzhou (CN)

( * ) Notice: Subject to any disclaimer, the term of this patent is extended or adjusted under 35 U.S.C. 154(b) by 559 days.

(21) Appl. No.: 17/272,369

(22) PCT Filed: Aug. 26, 2019

(86) PCT No.: PCT/CN2019/102443
§ 371 (c)(1),
(2) Date: Mar. 1, 2021

(87) PCT Pub. No.: WO2020/043033
PCT Pub. Date: Mar. 5, 2020

(65) Prior Publication Data

US 2021/0323971 A1 Oct. 21, 2021

(30) Foreign Application Priority Data

Aug. 31, 2018 (CN) ......................... 201811008444.4
Sep. 17, 2018 (CN) ......................... 201811083531.6

(51) Int. Cl.

| | |
|---|---|
| ***C07D 487/14*** | (2006.01) |
| ***C07D 207/08*** | (2006.01) |
| ***C07D 207/16*** | (2006.01) |
| ***C07D 241/20*** | (2006.01) |
| ***C07D 487/04*** | (2006.01) |

(52) U.S. Cl.
CPC ......... *C07D 487/14* (2013.01); *C07D 207/08* (2013.01); *C07D 207/16* (2013.01); *C07D 241/20* (2013.01); *C07D 487/04* (2013.01)

(58) Field of Classification Search
CPC .................................................... C07D 487/14
See application file for complete search history.

(56) References Cited

FOREIGN PATENT DOCUMENTS

| | | | | |
|---|---|---|---|---|
| CN | 108368121 A | | 8/2018 | |
| IN | WO 2020/202183 | * | 8/2020 | ........... C07D 207/16 |
| WO | 2011068881 A1 | | 6/2011 | |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*

* cited by examiner

*Primary Examiner* — Nizal S Chandrakumar

(57) ABSTRACT

The present disclosure relates to a JAK inhibitor upadacitinib intermediate and a preparation method therefor, and to a preparation method for a JAK inhibitor upadacitinib. The upadacitinib intermediate of the present application is as shown in Formula (II) or Formula (III),

II

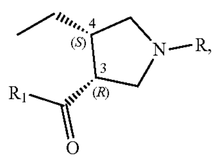

III

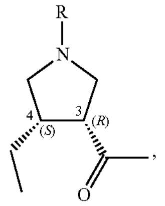

wherein, R is a protective group of nitrogen atoms, and $R_1$ is an open-chain or cyclic amine group. Compared with the prior art, the method for the synthesis of upadacitinib of the present application, significantly reduces cost, is environmentally-friendly. And the quality of the final product is well controlled.

2 Claims, No Drawings

SYNTHESIS METHODS FOR UPADACITINIB AND INTERMEDIATE THEREOF

TECHNICAL FIELD OF THE INVENTION

This application relates to the pharmaceutical synthesis field, in particular, to a JAK inhibitor upadacitinib intermediate and a preparation method therefor, and in addition, to a preparation method for a JAK inhibitor upadacitinib.

BACKGROUND OF THE. INVENTION

The specific causes of rheumatoid arthritis (RA) and psoriatic arthritis (PsA) are unknown, and it is presumed from medical practice that they have an important relationship with the partial defects of the patient's immune function. Rheumatoid arthritis has a long disease course, and because it is often with immune dysfunction, patients often die from complications such as cardiovascular diseases, infections and renal function impairment.

Currently, JAK inhibitors are one of the effective treatments for such immune system diseases. Among them, upadacitinib, as AbbVie's new drug for the treatment of rheumatoid arthritis and psoriatic arthritis, is a new JAK1 inhibitor JAK1 is a kinase, which plays a key role in the pathophysiologic processes of various inflammatory diseases including rheumatoid arthritis (RA), Crohn's disease (CD), ulcerative colitis (UC), psoriatic arthritis (PsA), etc. Currently, AbbVie is also evaluating the potential of upadacitinib to treat other immune diseases, including PsA, ankylosing spondylitis (AS) and atopic dermatitis. Currently, the New Drug Application (NDA) related to upadacitinib has been submitted to the US Food and Drug Administration (FDA).

So far, there are few reports on upadacitinib related patents. The main reported patent synthetic route is a synthetic route of the originator drugmaker AbbVie (WO2017066775A1):

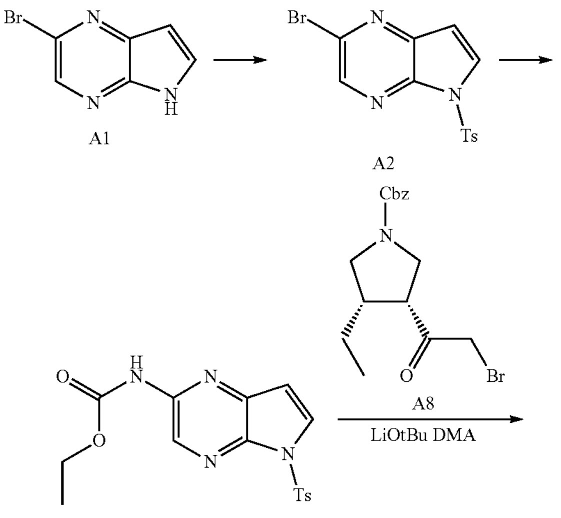

A3

-continued

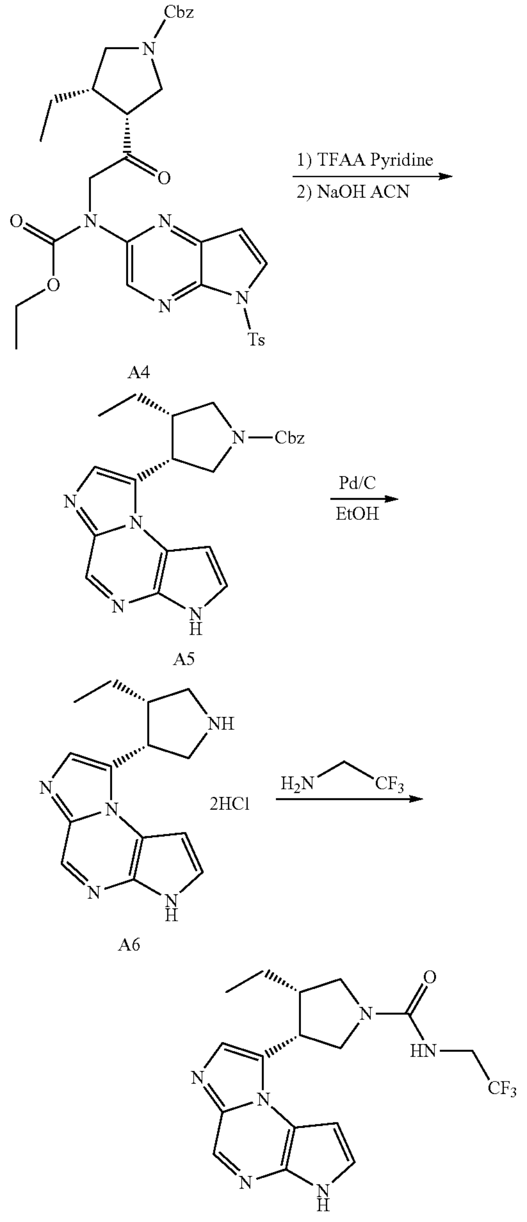

A7 (upadacitinib)

In WO2017066775, the synthesis method of Compound A8 in the above synthetic route is also disclosed, as shown below:

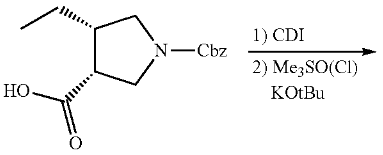

A10

-continued

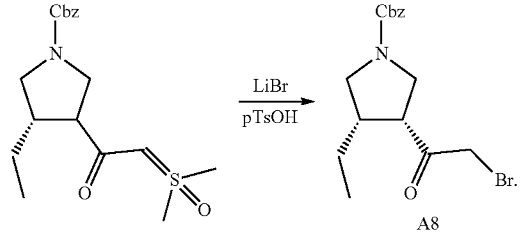

A9 A8

In addition, in a literature report (WO2013043826A1) earlier than WO2017066775A1, AbbVie also reported the synthesis of key Intermediate A8 through a diazo compound A11. The synthetic route is as follows:

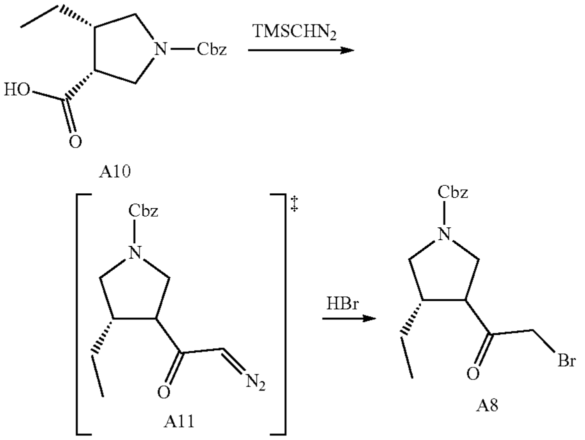

A10 A11 A8

There are disadvantages in the above two routes for the synthesis of Intermediate A8. Among them, the synthetic route reported in patent WO2013043826A1 uses TMS diazomethane as reagent, which is known to be highly toxic and poses safety risks in industrial scale-up production. The synthetic route reported in patent WO2017066775A1 uses Intermediate A9. Compound A9 and $Me_3SOCl$ are sulfur containing compounds, which are of bad odor. Moreover, the conversion of Compound A9 to Compound A8 affords a by-product with very bad smell. The process is not suitable for large scale production. Therefore, it is necessary to design a safer and more environmentally-friendly synthetic route.

In addition, with regard to Compound A1, a WO2017066775A1, WO2006058120A1, and CN106432246A disclosed the following synthesis method:

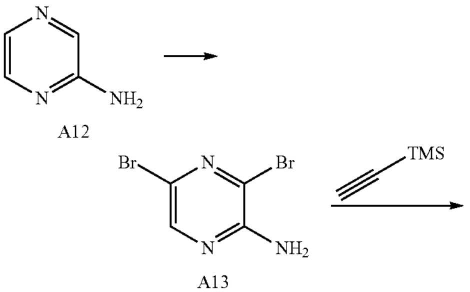

A12 A13

-continued

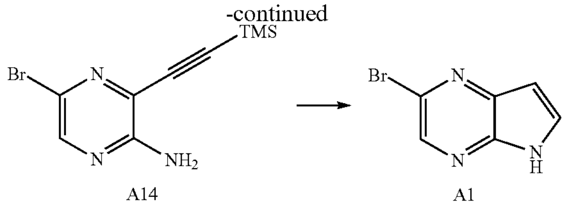

A14 A1

The synthesis method of A1 disclosed in WO2006058120A1 and CN106432246A used trimethylsilylacetylene as a synthetic building block. However, trimethylsilylacetylene is expensive.

In addition, in the route disclosed in WO2017066775A1, in the step of preparing Compound A7, namely upadacitinib from Compound A6, the disubstituted impurity A15 would inevitably for which made the purification of upadacitinib very difficult.

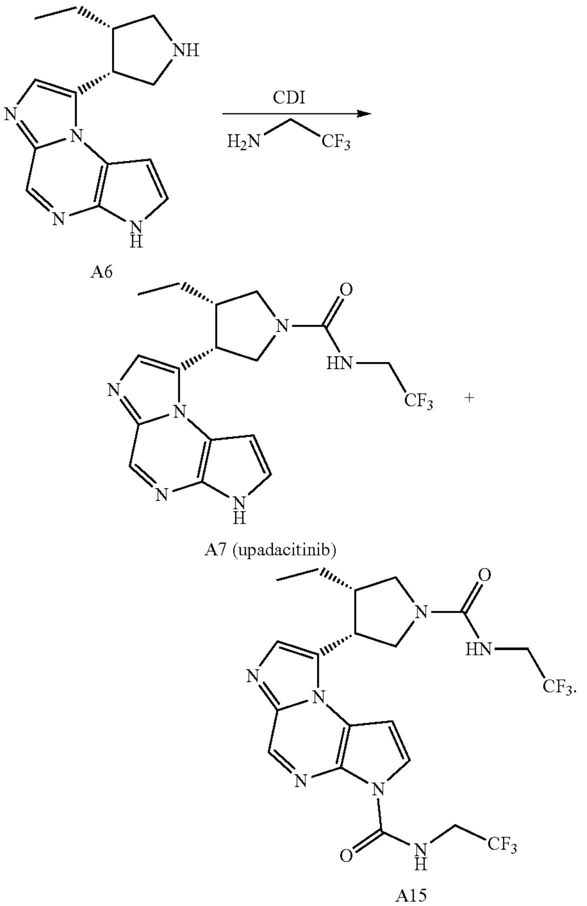

A6 A7 (upadacitinib) A15

In summary, the synthesis methods of upadacitinib in the prior art have disadvantages such as high cost, not environmentally-friendly, and involving the use of high toxic reagent. To develop a low-cost, environmentally-friendly, and efficient synthesis method of the JAK1 inhibitor upadacitinib is warranted.

SUMMARY OF THE INVENTION

The first purpose of this application is to provide a novel compound suitable as an intermediate for the synthesis of upadacitinib and a preparation method thereof.

The second purpose of this application is to provide a method for synthesizing key intermediates of upadacitinib using the provided novel compounds and finally synthesizing upadacitinib.

To achieve the above purpose, the present disclosure, on one hand, provides a compound, having a structure as shown in formula II:

II

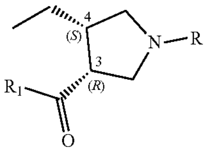

wherein, R is a protective group of nitrogen atom, and $R_1$ is an open-chain or cyclic amino group.

From the above structural formula, those skilled in the art would understand that Position 3 of the compound of formula II is the WO configuration, and Position 4 is the (S) configuration.

In regard to the protective group of nitrogen atoms, various types of protective groups known in the art can be selected, and there is no particular limitation. However, for the purposes of this application, preferred protecting groups are benzyl, benzyloxycarbonyl, and allyloxycarbonyl.

According to this application, the open-chain amino group generally refers to various chain-like amino groups, and the number of carbon atoms contained in the open-Chain amino group is usually 1 to 20, preferably 1 to 12, more preferably 1 to 6. The cyclic amino group generally refers to various cyclic amino groups, and may be a saturated or unsaturated ring, usually a 3- to 8-membered ring, preferably a 3- to 6-membered ring, and more preferably a 4-membered ring, a 5-membered ring or a 6-membered ring. The ring may contain heteroatoms other than nitrogen such as oxygen atoms.

According to some aspects of this application, in Formula II, $R_1$ is selected from the group consisting of C1-6 akylamino, C1-6 alkoxyamino, C1-6 alkyl C1-6 alkyl his-substituted amino, C1-6 alkoxy C1-6 alkoxy bis-substituted amino. C1-6 alkoxy C1-6 alkyl his-substituted amino, wherein C1-6 alkyl may specifically be methyl, ethyl, propyl, isopropyl and the like. Preferably, $R_1$ is selected from the group consisting of C1-3 alkylamino, C1-3 alkoxyamino, C1-3 alkyl C1-3 alkyl dis-substituted amino, C1-3 alkoxy C1-3 alkoxy dis-substituted amino. C1-3 alkoxy C1-3 alkyl dis-substituted amino. Representative $R_1$ comprises, but is not limited to, methylamino, ethylamino, dimethylamino, diethylamino, methylethylamino, methoxyamino, ethoxy amino, dimethoxyamino, diethylaminoamino, methyl methoxyamino, methyl ethoxyamino, ethyl ethoxyamino, ethyl methoxyamino, and the like.

According to other aspects of this application, in Formula II, $R_1$ is selected from the group consisting of nitrogen-containing four-membered heterocyclic groups, nitrogen-containing five-membered heterocyclic groups, and nitrogen-containing six-membered heterocyclic groups, and the nitrogen atom contained in the nitrogen-containing four-membered heterocyclic groups, the nitrogen-contained five-membered heterocyclic groups and the nitrogen-containing six-membered heterocyclic groups is connected to the carbon atom of the carbonyl in Formula II, and the rings of these heterocyclic groups independently contain or dos not contain oxygen atoms.

Preferably, $R_1$ is selected from the group consisting of nitrogen-containing four-membered heterocyclic groups, nitrogen-containing five-membered heterocyclic groups, and nitrogen-containing six-membered heterocyclic groups, and the rings of the nitrogen-containing four-membered heterocyclic groups, the nitrogen-containing five-membered heterocyclic groups and the nitrogen-containing six-membered heterocyclic groups respectively contains one oxygen atom, and the oxygen atom and the nitrogen atom on the ring are in non-adjacent positions.

According to some specific and preferred aspects of this application: in Formula II, $R_1$ is selected from the group consisting of morpholinyl, 1-methyl-1-methoxyamino, 1-ethyl-1-methoxyamino, 1-methyl-1-ethoxyamino, and 1-ethyl-1-ethoxyamino.

The typical compound. II has a structure described in Formula II-a or II-b:

II-a

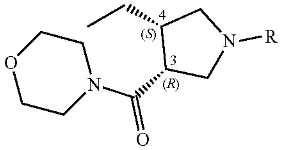

II-b

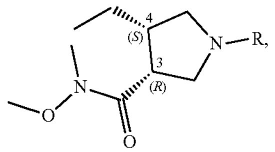

In Formula II-a or II-b, the definition of R is the same as previous.

This application further provides a synthesis method for Compound H, which comprises a step of reacting Compound I with a secondary amine compound to prepare Compound H, where the secondary amine compound is $R_1H$ or a salt thereof,

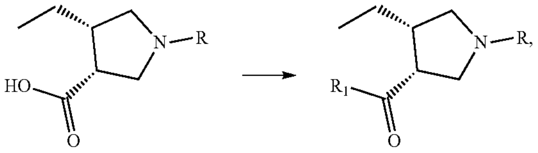

I II

The definitions of R and Pa in the formula are respectively the same as previous.

Specific examples of the secondary amine compound comprise morpholine, dimethylhydroxylamine hydrochloride and the like.

Those skilled in the art will understand that the compound of Formula II can be prepared from the compound of Formula I by condensation reaction methods known in the art, using such as DCC, EDC and other reagents to promote the dehydration condensation reaction.

Preferably, the reaction is carried out in the presence of O-(benzotriazol-1-yl)-N,N,N',N'-tetramethyluronium tetrafluoroborate and/or diisopropylethylamine.

Further preferably, the method comprises: (1) obtaining a mixed system containing Compound I, O-(benzotriazol-1-yl)-N,N,N',N'-tetramethyluronium tetrafluoroborate, a secondary amine compound and a solvent; (2) controlling the temperature of the mixed system at 0 to 10° C., adding diisopropylethylamine dropwise, after the dropwise addition is completed, heating up to room temperature to react.

The compound of Formula II obtained by the method of this application is a (3R,4S) chiral compound, and the isomer content of the target compound in the obtained product is not higher than 20%.

Preferably, a charge molar ratio of Compound I, the secondary amine compound, O-(benzotriazolyl)-N,N,N',N'-tetramethyluronium tetrafluoroborate and diisopropylethylamine is 1:1:1:1 to 1:2:2:3.

The present disclosure also relates to a compound (Compound III) with a structure shown in Formula III:

III

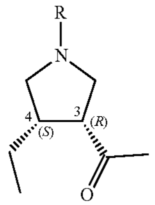

wherein, R is a protective group of nitrogen atoms.

From the above structural formula, those skilled in the art will understand that Position 3 of the compound of formula III is the (R) configuration, and Position 4 is the (S) configuration.

In regard to the protective, group of nitrogen atoms, various types of protective groups known in the art can be Selected, and there is no particular limitation. However, for the purposes of this application, preferred protecting groups are benzyl benzyloxycarbonyl, and allyloxycarbonyl.

This application further provides a synthesis method for Compound III, which comprises a step of reacting Compound II described in the present application with a methyl metal reagent to prepare Compound III:

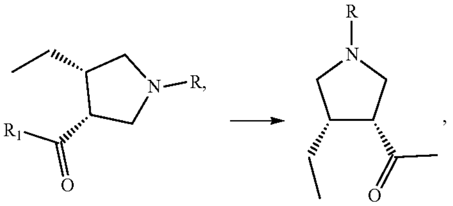

II III

The definitions of R and $R_1$ in the formula are respectively the same as previous.

Preferably, the methyl metal reagent is selected from the group consisting of methyl lithium reagents and methyl Grignard reagents. The methyl Grignard reagent may specifically be, for example, methyl magnesium bromide.

The compound of Formula III obtained by the method of this application is a (3R,4S) chiral compound, and the isomer content of the target compound in the obtained product is not higher than 70%.

It is known that the compound of Formula IV is one of the important intermediates for the synthesis of upadacitinib. This application further provides a synthesis method for Compound IV which comprises a step of reacting Compound III described in the present application with a brominating reagent to prepare Compound IV,

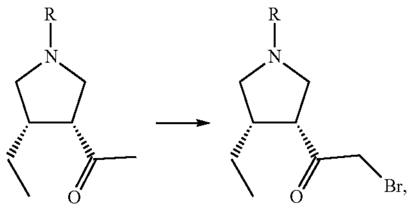

III IV the definition of R in the formula is the same as previous.

Further, the method further comprises a step of obtaining Compound III by the method for preparing Compound III described in this application, and/or a step of obtaining Compound II by the method for preparing Compound. II described in this application.

This application further provides a synthesis method for upadacitinib, which comprises a step of preparing tire compound of Formula IV by the synthesis method for the compound of Formula IV described in this application.

Further, the synthesis method for upadacitinib further comprises a step of preparing Compound VII, and the step of preparing Compound VII comprises removing acetone from Compound VI under basic conditions followed by ring-closing to afford Compound VII:

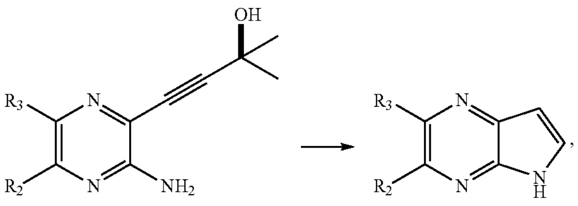

VI VII

The $R_2$ is hydrogen, fluorine, chlorine, bromine, iodine or a C1-20 hydrocarbon; P3 is hydrogen, fluorine, chlorine, bromine, iodine or a C1-20 hydrocarbon; X is bromine or iodine.

The C1-20 hydrocarbon generally refers to a C1-20 hydrocarbyl, preferably a C1-20 alkyl, more preferably a C1-12 alkyl, and even more preferably a C1-6 alkyl.

Further, the step of preparing Compound VII further comprises causing Compound V and 2-methyl-3-butyn-2-ol to undergo a coupling reaction under the catalysis of a transition metal catalyst to produce Compound VI:

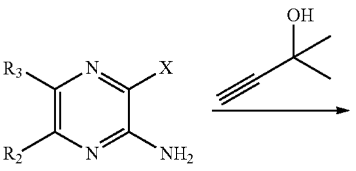

V

-continued

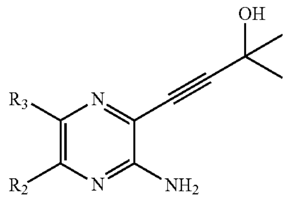

,

VI

The definitions of $R_2$ and $R_3$ are respectively the same as previous; X is bromine or iodine.

Further, the basic condition is formed by adding one or more bases selected from the group consisting of sodium hydroxide, potassium hydroxide, potassium tert-butoxide, and sodium hydride.

Further, the transition metal catalyst may be selected from the group consisting of a palladium catalyst and a copper catalyst.

According to a specific aspect of this application, the $R_2$ is hydrogen and $R_3$ is bromine; R in the compound of Formula IV is benzyloxycarbonyl.

The method for preparing Compound VII in this application has a yield comparable to the existing method. And at the same time, because 2-methyl-3-Butyn-2-ol is a relatively low-cost material, compared with the expensive trimethylsilyl acetylene used in the prior art, the cost of upadacitinib prepared by the synthetic method of this application is significantly reduced.

Further, the synthetic method for upadacitinib further comprises a step of deprotecting Compound XII to obtain Compound XIII, and a step of causing Compound XIII, N,N'-carbonyldiimidazole, 2,2,2-trifluoroethylamine to react and produce Compound XIV:

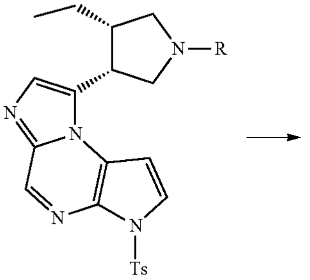

XII

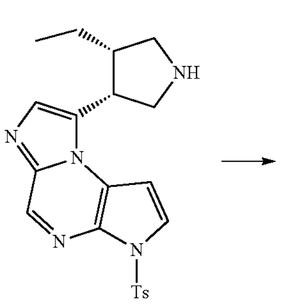

XIII

-continued

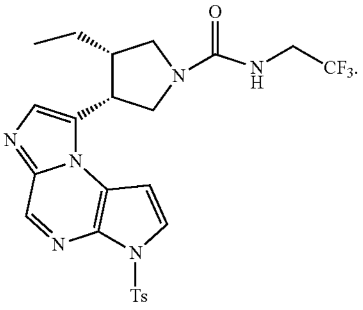

XIV

In the above formula, Ts represents 4-toluenesulfonyl, and the definition of R is the same as previous.

The synthesis method for the above Compound XIV can effectively avoid the formation of di-substituted impurities in the last step of the synthesis of the active pharmaceutical ingredients (API), which is of great significance for the preparation of high quality API.

According to a specific aspect of this application, upadacitinib (Compound 18) is synthesized via the following synthetic route:

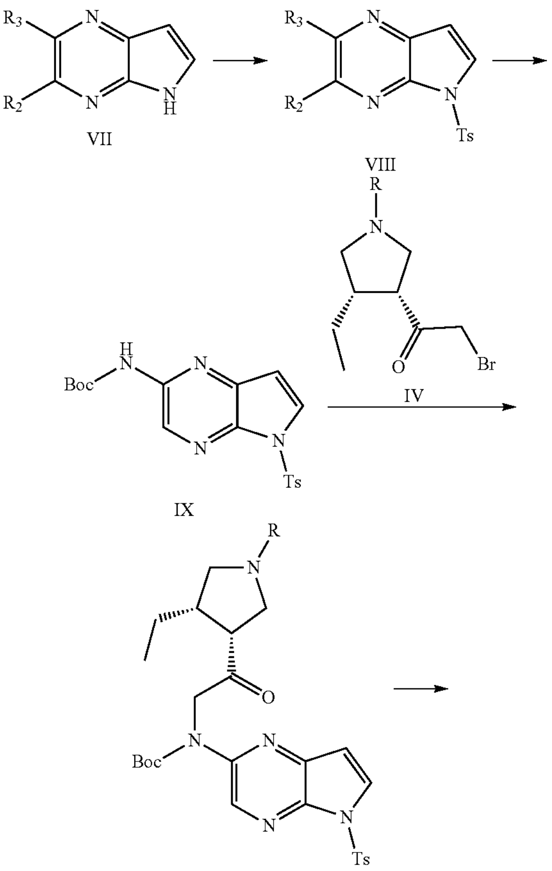

VII VIII IX IV X

-continued

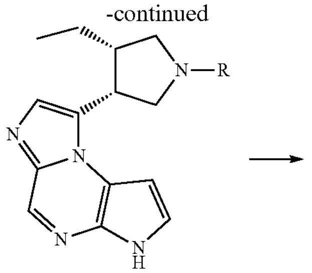

XI

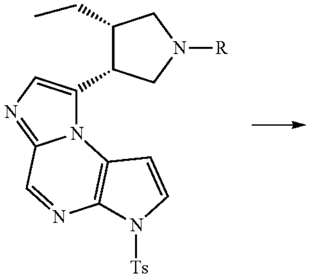

XII

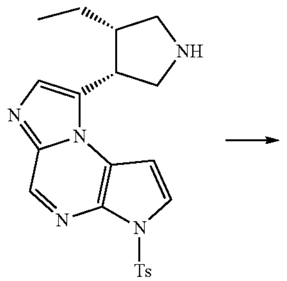

XIII

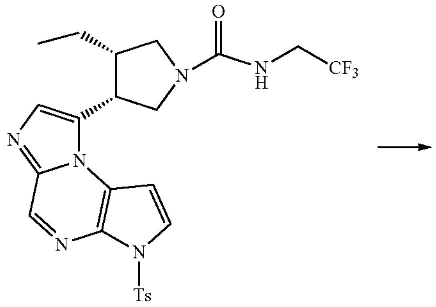

XIV

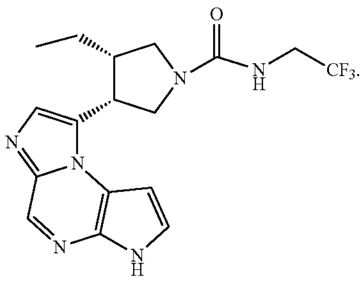

18

Compared with the prior art, the method for the synthesis of upadacitinib of the present application significantly reduces cost, and is environmentally-friendly. And the quality of the final product is well controlled.

DETAILED DESCRIPTION OF EXEMPLARY EMBODIMENTS

The following embodiments describe the implementation of the present application, and those skilled m the art should realize that these specific embodiments only show the implementation technical solutions selected to achieve the purpose of this application, and are not limitations on the technical solutions. According to the teaching of this application, the improvement of the technical solution of this application in combination with the prior art is obvious, which all fall within the protection scope of this application.

The implementation conditions employed by the embodiments may be further adjusted according to particular requirements, and undefined implementation conditions usually are conditions in conventional experiments.

Among them, the brown chemical reagents used in the following embodiments are all commercially available chemical reagents or can be prepared by referring to the methods in WO2013043826A1 and WO2017066775A1.

In the exemplary implementations of the present disclosure, those skilled in the art can also make changes to the synthetic route, for example, change specific reaction conditions or adjust a certain step or several steps of the synthetic route as needed. Any changes made without departing from the substance of this application are within the protection scope of this application.

Abbreviations: TsCl: 4-toluenesulfonyl chloride; Cbz: benzyloxycarbonyl protective group; TBTU: O-(benzotriazol-1-yl)-N,N,N',N'-tetramethyluronium tetrafluoroborate; X-Phos: 2-dicyclohexylphosphorus-2',4',6'-triisopropylbiphenyl; Boc anhydride: di-tert-butyl dicarbonate; CDI: N,N'-carbonyldiimidazole.

Embodiment 1

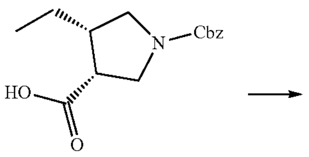

1

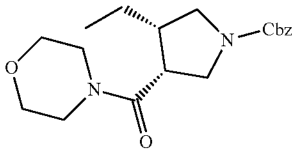

2

To a 100 mL three-necked flask were added 2.2 g of Compound 1, 22 mL of dichloromethane, 3.82 g of TBTU, and 1.38 g morpholine under N protection, the temperature was cooled to 0 to 10° C. 1.54 g of diisopropylethylamine was added dropwise. The reaction mixture was warmed to room temperature and was held for 1 h. Upon completion, 11 mL of water was added. The layers were separated. The aqueous phase was extracted with 22 ml dichloromethane. The organic phases were combined, washed with 6.6 mL of brine, concentrated under vacuum. The crude product was purified by silica gel column chromatography to give 2.35 g of light yellow oil, namely Compound 2, with a yield of 87.0%.

The NMR data of Compound 2 are as follows: $^1H$ NMR (400 MHz, $CDCl_3$) δ 7.36-7.34 (m, 5H), 5.15-5.11 (m, 2H), 3.83-3.27 (m, 13H), 2.26-2.19 (m, 1H), 1.39-1.35 (m, 2H), 0.95-0.89 (m, 3H).

The mass spectrum data of Compound 2: $[M+H]^+$ 347.4.

Embodiment 2

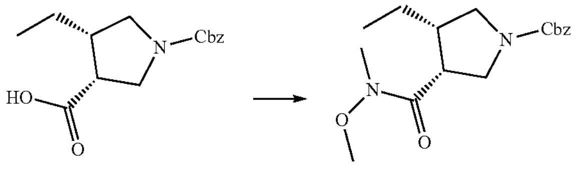

1 3

To a 10 mL three-necked flask were added 120 rug of Compound 1, 84 mg of dimethylhydroxylamine hydrochloride, 209 mg of TBTU, and 1.8 mL of dichloromethane under $N_2$ protection. The reaction was cooled to 0 to 10° C. 140 mg of diisopropylethylamine was added dropwise. The reaction mixture was warmed to room temperature and was held for 1 h. Upon reaction completion, 1 mL of water was added. The layers were separated. The aqueous phase was extracted with 10 mL of dichloromethane. The organic phases were combined, washed with 1 mL of brine, concentrated under vacuum. The crude product was purified by silica gel column chromatography to give 105 mg of light yellow oil Compound 3, with a yield of 76.1%.

The NMR data of Compound 3 are as follows: $^1H$ NMR (400 MHz, $CDCl_3$) δ 7.38-7.31 (m, 5H), 5.18-5.08 (m, 2H), 3.76-3.72 (m, 1H), 3.69 (s, 3H), 3.62-3.34 (m, 4H), 3.18 (s, 3H), 3.39-3.33 (m, 1H), 1.33-1.25 (m, 2H), 0.93-0.88 (m, 3H).

Embodiment 3

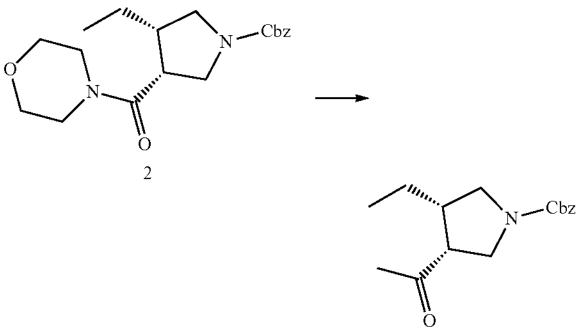

2

4

To a 100 mL three-necked flask were added 1.4 g of Compound 2 and 14 mL of tetrahydrofuran under $N_2$ protection. The reaction mixture was cooled to below −60° C. 3.8 mL of methyl lithium solution in tetrahydrofuran (1.6 M) was added dropwise. Upon reaction completion, 10 mL of saturated ammonium chloride was added. The mixture was warmed to room temperature. 15 MT of ethyl acetate was added. The layers were separated. The aqueous phase was extracted with 15 mL of ethyl acetate. The organic phases were combined, washed with 5 mL of brine, concentrated under vacuum. The crude product was purified by silica gel column chromatography to give 710 mg of light yellow oil Compound 4, with a yield of 645%.

The NMR data of Compound 4 are as follows: $^1H$ NMR (400 MHz, $CDCl_3$) δ 7.37-7.30 (m, 5H), 5.15-5.12 (m, 2H), 3.72-3.65 (m, 1H), 3.58-3.19 (m, 4H), 2.38-2.34 (m, 1H), 2.18 (s, 3H), 1.40-1.26 (m, 2H), 0.96-0.91 (m, 3H).

Embodiment 4

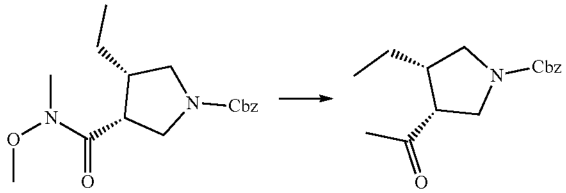

3 4

To a 10 mL three-necked flask were added 90 mg of Compound 3 and 1.8 mi of tetrahydrofuran under $N_2$ protection. 0.3 ml of methyl lithium solution in tetrahydrofuran (1.6 M) was added dropwise at below −60° C. Upon reaction completion, 2 mL of saturated ammonium Chloride was added. The mixture was warmed to room temperature. 5 mL of ethyl acetate was added. The layers were separated. The aqueous phase was extracted with 10 mL of ethyl acetate. The organic phases were combined, washed with 5 mL of brine, concentrated under vacuum. The crude product was purified by silica gel column chromatography to give 70 mg of light yellow oil Compound 4, with a yield of 90.9%.

The NMR data of Compound 4 are as follows: $^1H$ NMR (400 $CDCl_3$) δ 7.37-7.30 (m, 5H), 5.15-5.12 (m, 2H), 3.72-3.65 (m, 1H), 3.58-3.19 (m, 4H), 2.38-2.34 (m, 1H), 2.18 (s, 3H), 1.40-1.26 (m, 2H), 0.96-0.91 (m, 3H).

Embodiment 5

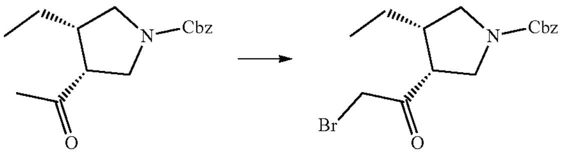

4 5

To a 10 mL three-necked flask were added 200 mg of Compound 4, 2.0 mL of methanol, 440 mg of 40% HBr aqueous solution, and 697 rug of bromine under $N_2$ protection. The reaction mixture was stirred at room temperature. Upon reaction completion, 2 mL of saturated sodium thiosulfate aqueous solution was added, and saturated sodium bicarbonate aqueous solution was added to adjust the pH to 7, then 10 mL ethyl acetate was added. The lavers were separated. The aqueous phase was extracted twice with 10 mL of ethyl acetate (10 mL each time). The organic phases were combined, concentrated under vacuum. The crude product was purified by silica gel column chromatography to give 182 mg of light yellow oil. Compound 5, with a yield of 70.7%;

The mass spectrum data of Compound 5: $[M+H]^+$ 354.1.

Embodiment 6

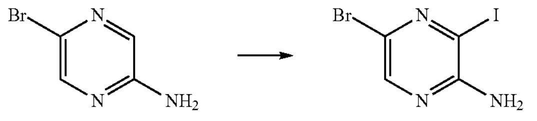

6 7

To a 25 mL round-bottom flask were added 5 (0.2 of Compound 6, 7.5 mL of acetonitrile, and 2.7 g of acetic acid. To another 100 mL three-necked flask were added 6.8 mL of acetonitrile, 1.8 g of acetic acid, and 3.1 g of iodine, 6.1 g of 20% sulfuric acid and 3.2 g of sodium iodate was added at 65-75° C. To the 100 mL three-necked flask were added the mixed solution in the 25 mL single-necked flask dropwise. The reaction mixture was warmed to 75 to 85° C. Upon reaction completion, the system was cooled to 60 to 70° C. To the solution reaction mixture were added 15 g of 40% $NaHSO_3$ aqueous solution, 30 of water, and 17 g of 30% NaOH aqueous solution. After being cooled to 0 to 10° C., the mixture was filtered. The cake was recrystallized in toluene to give 4.6 g of Compound 7, with a yield of 54.0%.

The mass spectrum data of Compound 7: $[M+H]^+$ 299.9.

Embodiment 7

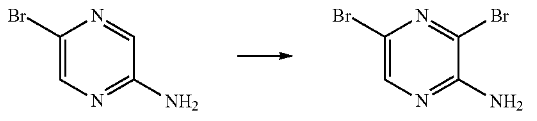

6 8

To a 250 mL three-necked flask were added 10 g of Compound 6, 15.3 g of N-bromosuccinimide, and 100 mg of 1,4-dioxane under $N_2$ protection at room temperature. Upon reaction completion, 20 mL of saturated sodium thiosulfate aqueous solution was added. The layers were separated. The aqueous phase was extracted with 50 ml of dichloromethane. The organic phases were combined, washed with 10 of brine, concentrated under vacuum to give crude Compound 8, which was recrystallized from n-heptane and ethyl acetate to give 7.1 g of Compound 8, with a yield of 72%;

The mass spectrum data of Compound 8: $[M+H]^+$ 251.9.

Embodiment 8

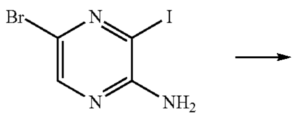

7

-continued

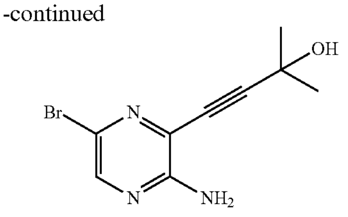

9

To a 25 mL three-necked flask were added 0.82 g of Compound 7, 0.43 g of triethylamine, 4 mL of dichloromethane, and 250 mg of methyl butanol under $N_2$ protection. 7.7 rug of CuCl and 22.7 mg of $PdCl_2(PPh_3)_2$ were added. The reaction system was refilled with $N_2$ for three times. The reaction was stirred at 20 to 30° C., for 12 h. Upon completion, 5 mi, of water and 20 mL of dichloromethane were added. The layers were separated, the organic phase was concentrated. The crude product was purified by silica gel column chromatography to give 0.54 g of Compound 9, with a yield of 77%.

The NMR data of Compound 9 are as follows: $^1H$ NMR (400 MHz, d-DMSO) δ 8.08 (s, 1H), 6.75 (s, 2H), 5.66 (s, 1H), 1.49 (s, 6H).

The mass spectrum data of Compound 9: $[M+H]^+$ 756.1.

Embodiment 9

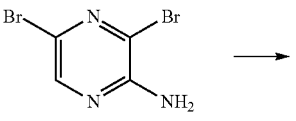

8

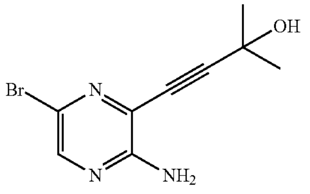

9

To a 150 mL three-necked flask were added 5 g of Compound 8, 2.4 g of triethylamine and 25 mL of 1,4-dioxane under $N_2$ protection. 0.182 g of CuCl, 120 mg of $PdCl_2(PPh_3)_2$ and 2.0 g of methyl butanol was added. The reaction was refilled with $N_2$ for three times. The reaction was stirred at 75° C. for 12 h. Upon completion, the solution reaction mixture was cooled to room temperature. 74 ml of 1 N hydrochloric acid and 25 oil, of dichloromethane were added. The layers were separated. The aqueous phase was washed with 25 mL of dichloromethane. 12 g of 30 wt % NaOH aqueous solution was added to the aqueous phase. The resulting suspension was filtered to give 4.9 g of Compound 9, with a yield of 96%.

The NMR data of Compound 9 are as follows: $^1H$ NMR (400 MHz, d-DMSO) δ 8.08 (s, 1H), 6.75 (s, 2H), 5.66 (s, 1H), 1.49 (s, 6H).

The mass spectrum data of Compound 9: $[M+H]^+$ 256.1.

Embodiment 10

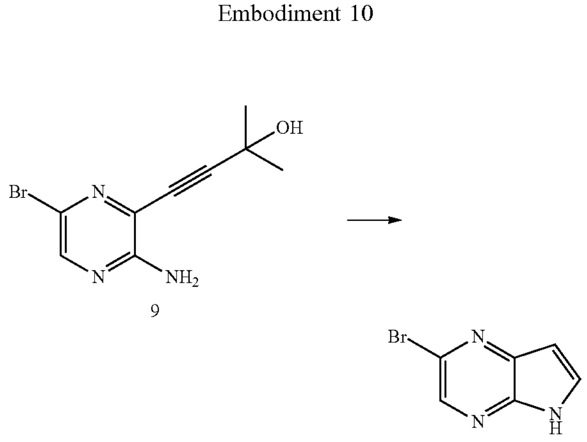

9

10

To a 10 mL three-necked flask were added 200 rug of Compound 9, 1.0 mL of N-methylpyrrolidone, and 0.9 g of 10 wt % NaOH aqueous solution under $N_2$ protection. The reaction was stirred at 70° C. Upon completion, the reaction mixture was cooled to room temperature, stirred for 2 h. The resulting suspension was filtered. The solid was dried to give 100 mg of Compound 10, with a yield of 65%.

The NMR data of Compound 10 are as follows: $^1H$ NMR (400 MHz, d-DMSO) δ 12.38 (br, 1H), 8.39 (s, 1H), 8.00 (m, 1H), 6.67 (m 1H).

Embodiment 11

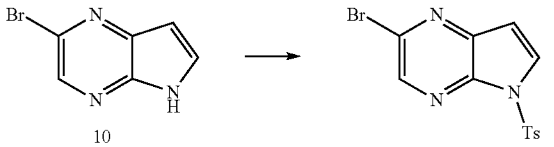

10

11

To a 1000 mL three-necked flask were added 65 g of Compound 10 and 260 mL, of N,N-dimethylformamide under $N_2$ protection. 15.7 g of NaH was added portion wise at 0 to 10 After 1 h, a solution of 75.1 g of TsCl in 260 mL N,N-dimethylfomamide was added at 0-10° C. Upon completion, 520 ml of water was added. The resulting suspension was stirred for 2 h. Filtration and recrystallized from ethyl acetate and n-heptane to give 99.0 g of Compound 11, with a yield of 86.1%.

The NNW, data of Compound 11 are as follows: $^1H$ NMR (400 MHz, d-DMSO) δ 8.58 (s, 1H), 8.37-8.36 (m, 1H), 8.00-7.98 (dd, 2H), 7.45-7.42 (m, 2H), 7.02-7.01 (m, 1H), 2.34 (s, 3H).

The mass spectrum data of Compound 11: $[M+H]^+$ 353.2.

Embodiment 12

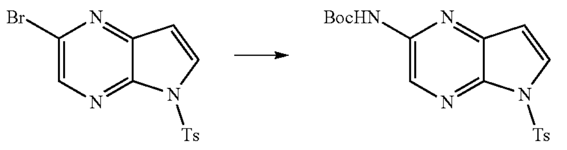

11

12

To a 1000 ml three-necked flask were added 50 g of Compound 11, 500 rant of toluene, 58.9 g of potassium carbonate, 50 g of tart-butyl carbamate. 637 mg of palladium acetate. 2.7 g of X-Phos, and 31 g of Boc anhydride. The system was refilled with $N_2$ for six times. The reaction was stirred at 90-100° C. Upon completion, the reaction mixture was cooled to 50-60° C. and was filtered. The filtrate was concentrated and purified by silica gel column chromatography to give 46.1 g of Compound 12, with a yield of 83.6%.

The NMR data of Compound 12 are as follows: $^1H$ NMR (400 MHz, d-DMSO) δ 9.08 (s, 1H), 8.05-8.03 (m, 2H), 7.93-7.92 (m, 1H), 7.49 (s, 1H), 7.30-7.28 (m, 1H), 6.63-6.62 (m, 1H), 4.51 (s, 1H), 2.39 (s, 3H), 1.54 (s, 9H).

Embodiment 13

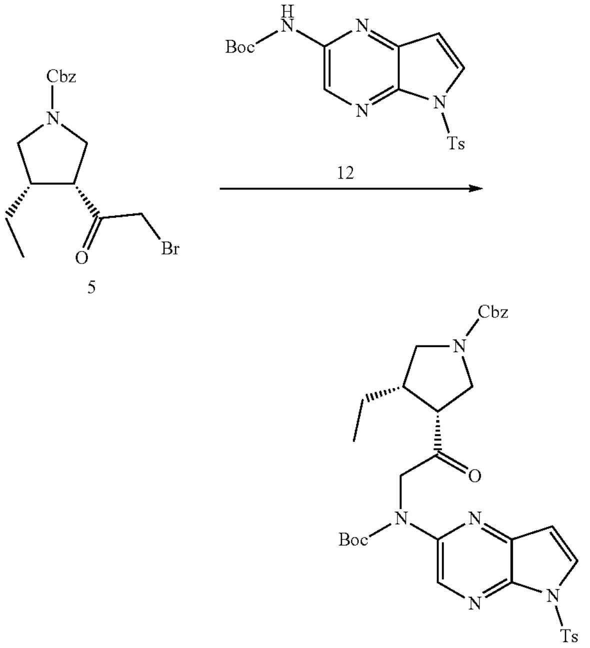

12

5

13

To a 500 mL three-necked flask were added 39.5 g of Compound 12 and 180 mL of N,N-dimethylacetamide under nitrogen protect. 8.96 g of lithium tert-butoxide was added at 5° C. After 1 h, the system was cooled to −15° C. A solution of 39.1 g of Compound 5 in N,N-dimethylacetamide (180 mL) was added dropwise at −20 to −10° C. After 1 h, 17.03 g of acetic acid was added. The reaction mixture was stirred at room temperature for 0.5 h. 360 of water and 360 ml of isopropyl acetate were added. The layers were separated. The aqueous phase was extracted once with 180 mL of isopropyl acetate. The organic phases were combined, and washed twice with 180 mL of 4% sodium bicarbonate solution, once with 180 mL of water. The organic phase was concentrated under reduced pressure, added 468 mL of methanol, then the mixture was warmed to 35'C, stirred for 0.5 h, then added 70 mg seed, stirred for another 0.5 h. added 54 mL of water, and stirred overnight. The resulting suspension was filtered. The solid was dried to give 42.08 g of Compound 13, with a yield of 62.57%.

The NMR data of Compound 13 are as follows: $^1H$ NMR (400 MHz, d-DMSO) δ 8.74 (s, 1H), 8.21-8.17 (m, 1H), 8.00-7.97 (m, 2H), 7.44-7.42 (m, 2H), 7.34-7.27 (m, 5H), 6.79-6.66 (m, 1H), 5.06-5.05 (m, 2H), 4.74 (s, 2H), 3.65-3.58 (m, 1H), 3.52-3.43 (m, 3H), 3.21-3.16 (m, 1H), 2.40-2.38 (m, 1H), 2.34 (s, 3H), 1.29-1.46 (m, 10H), 1.29-1.23 (m, 1H), 0.91-0.86 (m, 3H).

Embodiment 14

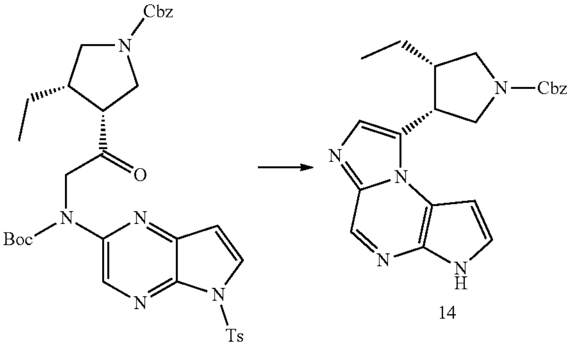

13 14

To a 500 mL three-necked flask were added 30 g of Compound 13-180 mL of acetonitrile, 38.1 g of trifluoroacetic anhydride, and 9.7 g. of pyridine. The reaction mixture was stirred at 70-80° C. for 2 h. The reaction solution was concentrated under reduced pressure. 210 mL of 2-methyltetrahydrofuran and 210 g of 20 wt % NaOH aqueous solution were added. The mixture was heated to 45-55° C. for 2 hours. After being cooled to room temperature, the layers were separated. The organic phase was washed with 105 g of saturated brine. After being concentrated under reduced pressure, the crude product was purified by silica gel column chromatography to give 15.8 g of Compound 14, with a yield of 90.0%.

The NMR data of Compound 14 are as follows: $^1H$ NMR (400 MHz, d-DMSO) δ 12.30 (s, 1H), 8.59 (s, 1H), 7.58-7.57 (m, 1H), 7.45-7.31 (m, 6H), 7.00-6.97 (m, 1H), 5.15-5.13 (m, 2H), 4.39-4.34 (m, 1H), 3.93-3.71 (m, 3H), 3.34-3.28 (m, 1H), 2.57-2.50 (m, 1H), 1.09-1.02 (m, 1H), 0.91-0.83 (m, 1H), 0.63-0.58 (m, 3H).

The mass spectrum data of Compound 14: $[M+H]^+$ 390.2.

Embodiment 15

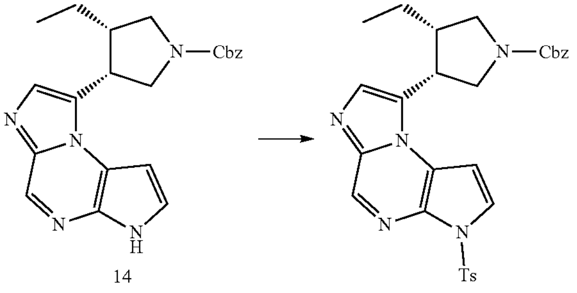

14 15

To a 100 mL three-necked flask were added 6 g of Compound 14 and 60 mL of tetrahydrofuran under $N_2$ protection, 3.46 mL of potassium tert-butoxide was added portion wise at 0-10° C. After 1 h, 4.4 g p-toluenesulfonyl chloride was added. Upon completion, 1.85 g of acetic acid was added, followed by the addition of 30 mL of water and 60 mL of ethyl acetate. The layers were separated. The organic phase was washed with 30 ml of saturated brine and concentrated. The crude product was purified by silica gel column chromatography to give 7.0 g of Compound 15, with a yield of 83.0%.

The NMR data of Compound 15 are as follows: NMR (400 MHz, d-DMSO) δ 8.77 (s, 1H), 8.04-8.02 (m, 2H), 7.98-7.97 (m, 1H), 7.70-7.69 (m, 1H), 7.44-7.29 (m, 1H), 5.16-5.08 (m, 2H), 4.35-4.30 (m, 1H), 3.87-3.70 (m, 3H), 3.34-3.27 (m, 1H), 2.47-2.46 (m, 1H), 2.33 (s, 3H), 0.99-0.94 (m, 1H), 0.88-0.82 (m, 1H), 0.60-0.55 (m, 3H).

The mass spectrum data of Compound 15: $[M+H]^+$ 544.1.

Embodiment 16

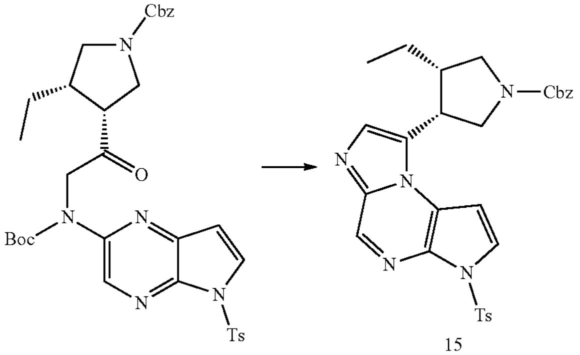

13 15

To a 25 mL three-necked flask were added 1 g of Compound 13, 10 mL of acetonitrile and 1.3 g of trifluoroacetic anhydride. The reaction mixture was stirred at 70-80° C. Upon completion, 5 mL of water and 30 mL of ethyl acetate was added. The layers were separated. The organic phase was washed with 10 mL of saturated brine and was concentrated. The crude product was purified by silica gel column chromatography to give 0.5 g of Compound 15, with a yield of 61.0%.

The NMR data of Compound 15 are as follows: $^1H$ NMR (400 MHz, d-DMSO) δ 8.77 (s, 1H), 8.04-8.02 (m, 2H), 7.98-7.97 (m, 1H), 7.70-7.69 (m, 1H), 7.44-7.29 (m, 1H), 5.16-5.08 (m, 2H), 4.35-4.30 (m, 1H), 3.87-3.70 (m, 3H), 3.34-3.27 (m, 1H), 2.47-2.46 (m, 1H), 2.33 (s, 3H), 0.99-0.94 (m, 1H), 0.88-0.82 (m, 1H), 0.60-0.55 (m, 3H).

The mass spectrum data of Compound 15: $[M+H]^+$ 544.1.

Embodiment 17

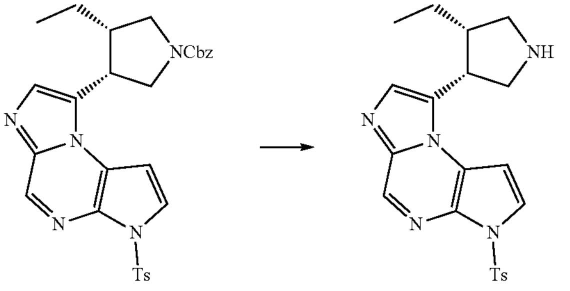

15 16

To a 25 mL three-necked flask were added 1 g of Compound 15, 15 mL of ethyl alcohol and 0.2 g of Pd/C. the reaction mixture was stirred under hydrogen atmosphere at 50-60° C. Upon completion, this solution was filtered. The filtrate was concentrated. The crude product was purified by silica gel column chromatography to give 315 mg of Compound 16, with a yield of 70.0%.

The NMR data of Compound 16 are as follows: $^1$H NMR (400 MHz, d-DMSO) δ 9.89 (br, 1H), 8.79 (s, 1H), 8.04-8.00 (m, 3H), 7.90 (s, 1H), 7.45-7.43 (m, 3H), 4.45-4.43 (m, 1H), 3.72-3.61 (m, 3H), 3.18-3.13 (m, 1H), 2.61-2.57 (m, 1H), 2.33 (s, 3H), 0.90-0.86 (m, 2H), 0.59-0.56 (m, 3H).

The mass spectrum data of Compound 16: $[M+H]^+$ 410.2.

Embodiment 18

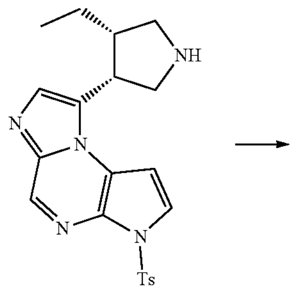

16

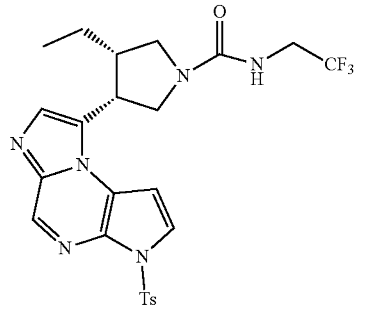

17

To a 25 mL three-necked flask were added 278 mg of CDI and 2.5 of tetrahydrofuran under $N_2$ protection. 182 mg of 2,2,2-trifluoroethylamine was added dropwise at 20-30° C. The mixture was stirred for 1 h. To another 25 mL three-necked flask were added 500 rag of Compound 16, 4 ml of tetrahydrofuran, 1 of water, 234 ma of dipotassium hydrogen phosphate. The pH was adjusted to 8 to 9.5 with 10 wt % KOH aqueous solution. To this solution was added the mixture in the first three-necked flask. The reaction was stirred for 2 h. Upon completion, 3 mi, of 20% citric acid and 10 of ethyl acetate were added. After being stirred at 20 to 30° C. for 1 h, the layers were separated. The organic phase was washed once with 5 mL of saturated brine and was concentrated. The crude product was purified by silica gel column chromatography to give 466 mg of Compound 17, with a yield of 71.5%.

The NMR data of Compound 17 are as follows: $^1$H NMR (400 MHz, d-DMSO) δ 8.77 (s, 1H), 8.05-8.03 (d, 2H), 7.99-7.97 (d, 1H), 7.59 (s, 1H), 7.46-7.43 (m, 3H), 6.94 (1, 1H), 4.34-4.29 (m, 1H), 3.88-3.65 (m, 5H), 3.27-3.23 (m, 1H), 2.46-2.54 (m, 1H), 2.35 (s, 3H), 1.04-0.99 (m, 1H), 0.82-0.77 (m, 1H), 0.63-0.60 (m, 3H).

Embodiment 19

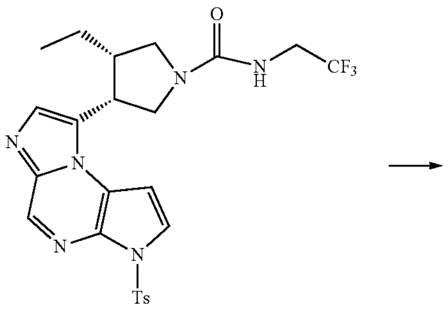

17

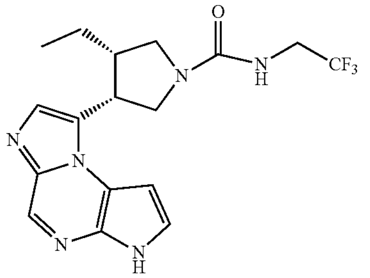

18

To a 25 mL three-necked flask were added 300 mg of Compound 17, 4.5 mL of 1,4-dioxane and 1.7 ml of 1N NaOH aqueous solution. The reaction mixture was stirred at 50-60° C. Upon completion, the reaction mixture was cooled to room temperature. 5 mL of water and 10 mL of ethyl acetate were added. The layers were separated. The aqueous phase was extracted once with 10 mL of ethyl acetate. The organic phases were combined, washed once with 10 mL of saturated brine, and was concentrated. The crude product was purified by silica gel column chromatography to give 186 mg of Compound 18, with a yield of 87.3%.

The NMR data of Compound 18 are as follows: Ili NMR (400 MHz, d-DMSO) δ 12.27 (s, 1H), 8.58 (s, 1H), 7.47-7.43 (m, 2H), 7.00-6.94 (m, 2H), 4.38-4.3.3 (m, 1H), 3.92-3.67 (m, 5H), 3.33-3.25 (m, 1H), 2.59-2.54 (m, 1H), 1.14-1.08 (m, 1H), 0.86-0.78 (m, 1H), 0.65-0.62 (m, 3H).

The mass spectrum data of Compound 18: $[M+H]^+$ 381.2.

This application includes but is not limited to the above embodiments. Any equivalent substitution or partial improvement made under the principle of the spirit of this application will be deemed to be within the protection scope of this application.

The invention claimed is:

1. A compound, having a structure shown Formula III:

III

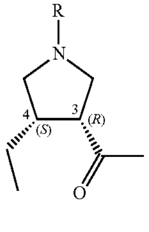

wherein, R is a protective group of nitrogen atoms.

2. The compound according to claim 1, wherein,
in Formula III, R is selected from the group consisting of benzyl, benzyloxycarbonyl, and allyloxycarbonyl.

* * * * *